(12) United States Patent
Vorage et al.

(10) Patent No.: US 7,618,664 B2
(45) Date of Patent: Nov. 17, 2009

(54) METHOD FOR PREPARING CALCIUM GLUCONATE

(75) Inventors: Marcus Johannes Anthonius Wilhelmus Vorage, Balloo (NL); Diderik Reinder Kremer, Groningen (NL); Boelem Sloots, Veendam (NL); Johannes Bernardus Maria Meiberg, Kropswolde (NL)

(73) Assignee: Cooperatieve Verkoop-en Productievereniging Van Aardappelmeel en Derivaten Avebe B.A., Ja Veendam (NL)

( * ) Notice: Subject to any disclaimer, the term of this patent is extended or adjusted under 35 U.S.C. 154(b) by 571 days.

(21) Appl. No.: 10/491,197

(22) PCT Filed: Oct. 7, 2002

(86) PCT No.: PCT/NL02/00603

§ 371 (c)(1), (2), (4) Date: Aug. 10, 2004

(87) PCT Pub. No.: WO03/031635

PCT Pub. Date: Apr. 17, 2003

(65) Prior Publication Data

US 2004/0253345 A1 Dec. 16, 2004

(30) Foreign Application Priority Data

Oct. 8, 2001 (EP) .................................. 01203793

(51) Int. Cl.
*A23L 1/00* (2006.01)
(52) U.S. Cl. ................................. 426/10; 426/7; 426/48
(58) Field of Classification Search ..................... 426/7, 426/10, 34, 42, 48, 74
See application file for complete search history.

(56) References Cited

U.S. PATENT DOCUMENTS 6,416,981 B1 * 7/2002 Chatterjee et al. ............ 435/137
6,828,130 B2 * 12/2004 Chatterjee et al. ............ 435/137
6,942,997 B2 * 9/2005 Lantero et al. ............... 435/136

FOREIGN PATENT DOCUMENTS

| ES | 8 609 192 | 12/1986 |
| GB | 1 299 646 | 12/1972 |
| WO | 00/28838 | 5/2000 |

OTHER PUBLICATIONS

Chem. Abstracts No. 218011 dated Dec. 7, 1987; Process for the Preparation of Calcium Lactate Gluconate.

* cited by examiner

*Primary Examiner*—Leslie Wong
(74) *Attorney, Agent, or Firm*—Lucas & Mercanti, LLP

(57) ABSTRACT

The invention provides for a method for the preparation of a gluconic acid from glucose. It is an aspect of the invention to provide a method that comprises the use of enzymes. The method according to the invention can be applied with great benefit to the production of calcium gluconate suitable for use as a food fortifier by a process that is economical.

23 Claims, 1 Drawing Sheet

METHOD FOR PREPARING CALCIUM GLUCONATE

This patent application claims the benefit of priority from European Patent Application No. 01203793.3 filed Oct. 8, 2001 through PCT Application Ser. No. PCT/NL2002/000603 filed Oct. 7, 2002, the contents of each of which are incorporated herein by reference.

The invention relates to the preparation of calcium gluconate by an enzymatic process.

BACKGROUND OF THE INVENTION

Micronutrients (vitamins and minerals) are not always present or available in sufficient amounts in foods. This may, inter alia, be due to specific deficits in the soil in which crops are grown, to a low bioavailability of the micronutrient, to unbalanced diets or to intestinal parasites. Recommended Nutrient Intakes (RNIs) or Recommended Daily Allowances (RDA) are aimed at informing the public about healthy levels of micronutrient intake.

It has been recognized that the intake of some nutrients at levels above the current RNIs may provide additional health benefits. Calcium intake levels above the RNIs are, for example, associated with increased bone mass in early adult life and in reduced risk of osteoporosis in later years.

Adequate calcium intake may be beneficial not only for the prevention and treatment of osteoporosis, but also for the reduction of risk of several diseases, including hypertension, colorectal cancer and oxalic renal calculi. Adolescents and the elderly are particularly vulnerable to the adverse effects of inadequate calcium intake. Recent studies and dietary recommendations have emphasized the importance of adequate calcium nutriture in pregnant women and in children, especially those undergoing the rapid growth and bone mineralization associated with pubertal development. The current dietary intake of calcium by children and adolescents in many parts of the world may well be below the recommended optimal levels.

While there is usually adequate calcium in the food supply to meet RNI levels, survey data indicate that many people are not consuming the recommended amounts of calcium. For example, many individuals do not consume milk products for a variety of health, cultural or personal reasons, and therefore have low intakes of calcium.

In order to alleviate micronutrient deficiencies, food fortification has become an essential element in nutrition strategies. An effective food fortification program improves the nutritional quality of a food supply by providing sources of essential nutrients and corrects inadequate intakes thereof.

Fortification, or enrichment, is defined as the addition of one or more vitamins or minerals to a food product irrespective of whether that food already contains that substance and concerns the vitamins A, B1, B2, B6, B12, C, D, E, K, niacin, folate, pantothenic acid and biotin and the minerals sodium, potassium, calcium, phosphorus, magnesium, iron, zinc, iodide, chloride, copper, fluoride, manganese, chromium, selenium, cobalt, molybdenum, tin, vanadium, silicon and nickel.

Food fortification is regulated by official governmental programs and is used as a tool for public health interventions (addition of iodine to salt), to restore nutrients lost during the processing of foods (addition of vitamin A to low fat or skim milk), to ensure the nutritional equivalence of substitute foods (addition of vitamin A to margarine) or to ensure the appropriate nutrient composition of special dietary foods such as meal replacements, nutritional supplements, low sodium foods, gluten-free foods, formulated liquid diets and sugar-free foods. Regulations determine which fortificants are allowable.

The presence of minerals like sodium, potassium, calcium and magnesium in the human diet is of eminent importance. Official documents state that for adults intakes of 1.1-3.3 gram/day sodium and 1.9-5.6 gram/day of potassium are estimated safe and adequate daily dietary intake levels. For calcium and magnesium, recommended daily allowances (RDA) are 0.8-1.2 gram/day and 0.3-0.4 gram/day, respectively. Sodium is generally present in sufficient levels and can easily be supplemented in the form of table salt. The situation for especially calcium is more complex.

In the human body calcium is primarily present in the bones and teeth (99%), and plays an important role in many enzymatic reactions in the intra- and extracellular fluids, blood clotting, muscle contraction, nerve transmission and in maintaining a regular heartbeat and blood pressure. Calcium is the most abundant mineral in the body and is predominantly present in the form of calcium phosphate. The bone acts as a large reservoir and buffer for $Ca^{2-}$ and $PO_4^{3-}$. Plasma levels of $Ca^{2-}$ and $PO_4^{3-}$ are held within narrow limits by a parathyroid peptide called parathyroid hormone (PTH) which increases bone calcium mobilization and intestinal absorption and decreases renal excretion of calcium, and a second peptide of thyroid origin, calcitonin, which has an opposite action by decreasing bone calcium release and by increasing calcium and phosphorous excretion by the kidney. Vitamin A is also involved, mainly in the intestinal absorption of calcium.

Daily losses of calcium must be replaced through dietary intake. Recognized sources of calcium are food sources (naturally occurring and/or as food fortificants), mineral supplements and miscellaneous sources such as antacids (for the treatment of gastric ulcers and acid reflux). The largest source of dietary calcium for most persons is milk (1.2-1.4 g calcium/liter) and other dairy products. Other sources of calcium are, however, important, especially for achieving calcium intakes of 1.2-1.5 g/day (US RNI). Most vegetables contain calcium, although at low density. Therefore, relatively large servings are needed to equal the total intake achieved with typical servings of dairy products.

Calcium adequacy depends not only on the quantity of intake, but also on the portion of calcium in food which can be absorbed through the intestines and is useable in the body, called bioavailability. Even if the daily food intake contains sufficient calcium to theoretically keep the balance of calcium in the body adequate, a lack of calcium in the body may occur. The bioavailability of calcium from vegetables is generally high. An exception is spinach, which is high in oxalate, making its calcium virtually non-bioavailable. Some high-phytate foods, such as whole bran cereals, may also have poorly bioavailable calcium.

While vitamin D and the parathyroid hormone are involved in the active intestinal absorption process, phosphates play a major role in the passive absorption based on diffusion. This absorption process is positively stimulated by the concentration of dissolved calcium: the greater the solubility of the calcium compound, the stronger the passive absorption.

Almost all calcium ingested and present in the stomach is essentially in ionic form because of the low pH conditions. However, when calcium enters the intestine the conditions are more neutral (pH 6-7 and the calcium may precipitate as insoluble calcium phosphate, depending upon the amount of phosphate present. The body is unable to absorb these precipitated calcium phosphates. Precipitation is most likely to occur when the calcium:phosphate ratio in the food or in the intestine is below 1. In Europe this ratio is around 0.6 and in the US this figure is even lower. Therefore, calcium supplementation of foods is beneficial for numerous reasons.

Several products have been introduced that are fortified with calcium. These products, most notably orange juice, are fortified to achieve a calcium concentration similar to that of milk. Limited studies suggest that the bioavailability of the calcium in these products is at least comparable to that of milk. The data on bioavailability of the various calcium fortificants are not conclusive. Several studies indicate equal bioavailability between calcium carbonate, calcium sulphate, calcium citrate and calcium lactate whereas other investigations show that organic calcium salts may possess higher bioavailability than inorganic salts such as calcium carbonate. Generally, bioavailability is determined by the solubility of a calcium compound as mentioned previously. Solubility is defined as the soluble concentration of a certain compound in water in the presence of the crystalline form of the compound, i.e. soluble and crystalline forms are in thermodynamic equilibrium.

The major problems involved in fortifying foods include the identification of suitable vehicles, selection of appropriate fortificant compounds, determination of technologies to be used in the production of the fortificant and in the fortification process and the influence on taste and consumer satisfaction of the food product. The selection of the appropriate calcium source for a specific fortification application is usually based on the consideration of a number of properties associated with the respective product such as taste, calcium content, bioavailability, absorbability (usually 10-40%), bioavailability and, most importantly in the case of calcium, solubility, which determines bioavailability and absorbability. Economic considerations are, evidently, other important factors. A calcium fortificant ideally exhibits a solubility in excess of 3 grams of $Ca^{2+}$ per liter.

Calcium carbonate, from oyster shells or limestone, is the most widely used calcium supplement because of its high calcium content and low cost. However, calcium carbonate has the disadvantage of developing $CO_2$ in the stomach, tends to produce a chalky mouthfeel, may impart a bitter, soapy or lemony taste on the finished product and may produce sediment in the food product. Most importantly, calcium carbonate is poorly soluble (<0.1 g/L at 25° C.) and therefore has a low absorption. Calcium phosphates, such as dicalcium phosphate impart a gritty mouthfeel, have a bland flavor and are also poorly soluble (<0.1 g/L at 25° C.).

Some organic calcium salts like calcium lactate, and calcium gluconate exhibit higher solubility and are better absorbed by the body. Tricalcium citrate offers a high calcium content and a neutral taste but is the least soluble (0.2 g/L at 25° C.). Calcium lactate, on the other hand, is highly soluble (9.3 g/L at 25° C.) making it very beneficial for obtaining a high calcium content in a food product. However, calcium lactate is perceived as bitter. Calcium gluconate is somewhat less soluble (3.5 g/L at 25° C.) as calcium lactate and it is considered to be one of the most neutral calcium salts with respect to taste allowing for high levels of addition in food products without negative impact on taste. Calcium gluconate is also very compatible with the human body. It does essentially not show any toxicity or astringency, and is therefore well tolerated.

Calcium gluconate is the calcium salt of gluconic acid. In order for the product to be registered as a food fortificant, it must be prepared at high purity, i.e without the presence of by-products that are unregistered. An important disadvantage of calcium gluconate is that it is relatively costly to produce. Several processes for the production of gluconates are described in the literature. U.S. Pat. No. 4,845,208 describes a process for the production of aldonic acids by aldose oxidation using a palladium-based catalyst. The disadvantage of this method is the use of very expensive and toxic catalysts and the formation of several by-products.

U.S. Pat. No. 5,102,795 describes the electrochemical oxidation of glucose to gluconic acid using sodium bromide and a neutralizing base. This method is presently used for production of gluconates but suffers from the problem that sodium bromide or bromide has to be separated from the final product.

A production process that generates gluconates of high purity (without the formation of by-products in the reaction mixture) is described in the international patent application 96/35800. In that publication, a combination of glucose oxidase and catalase enzymes is used to enzymatically convert glucose to gluconic acid while neutralizing with sodium hydroxide to obtain sodium gluconate at a yield close to 100% and practically without impurities. Sodium gluconate is highly soluble (380 g/L at 20° C.) and the inventors of that international patent application were able to achieve complete conversion of 273 g/L of glucose into gluconic acid (in the form of liquid sodium gluconate). Although the sodium ions may be exchanged by calcium ions to obtain calcium gluconate, such a process is impractical because of problems of calcium precipitation and the fact that a monovalent ion has to be exchanged for a divalent ion, attached to the resin, and industrial production of calcium gluconate in this way is unattractive. Moreover, ion exchange is an expensive unit operation and the process generates waste salts.

International patent application 97/24454 describes the enzymatic conversion of glucose into gluconic acid (in the form of liquid sodium gluconate) up to initial glucose concentrations of 450 g/L at a pH of 6,0 by using a pressurized reactor system and glucose oxidase from *Aspergillus niger* and catalase from *Micrococcus luteus*. However, this process does not allow for high yield productions of calcium gluconate since the solubility of calcium gluconate (30 g/L at 20° C.) is an order of magnitude lower than that of the corresponding sodium salt.

Also, calcium gluconate can be prepared by microbial fermentation as described by Shah and Kothari (Biotechnol. Lett. 1993; 15:35-40) and by Klewicki and Krol (Pol. J. Food Nutr. Sci. 1999; 8:71-79). The drawback of those procedures is related with the need to purify the calcium gluconate postproduction from by-products formed and to separate the micro-organisms from the product.

For the production of calcium gluconate an enzymatic process is preferred because of its high specificity and the resulting high purity of the product. However, the solubility of calcium gluconate under the conditions required for optimal enzymatic conversion (pH 5-7, 30-35° C.) is only 40 g/L. In order to obtain industrial quantities of the product, large reactors are needed and the concentration of the calcium gluconate crystals requires the evaporation of large amounts of water. Increase of the initial glucose concentration and instant crystallization of the formed calcium gluconate results in an increased viscosity of the reaction mixture and a concomitant decrease in the rates of oxygen transfer and enzymatic conversion. Intensification of agitation to restore oxygen transfer and overcome viscosity problems, e.g. by using Rushton turbines for stirring will raise equipment costs and heightens the risk of damage to the used equipment and concomitant metal contamination (chromium or nickel) of the final product. These drawbacks have rendered the enzymatic production of calcium gluconate on an industrial scale unattractive.

SUMMARY OF THE INVENTION

The present invention discloses a method to prevent the formation of crystals during enzymatic conversion of glucose into calcium gluconate rendering the enzymatic process for calcium gluconate production economically favorable.

DETAILED DESCRIPTION OF THE PREFERRED EMBODIMENT

Figure 1:
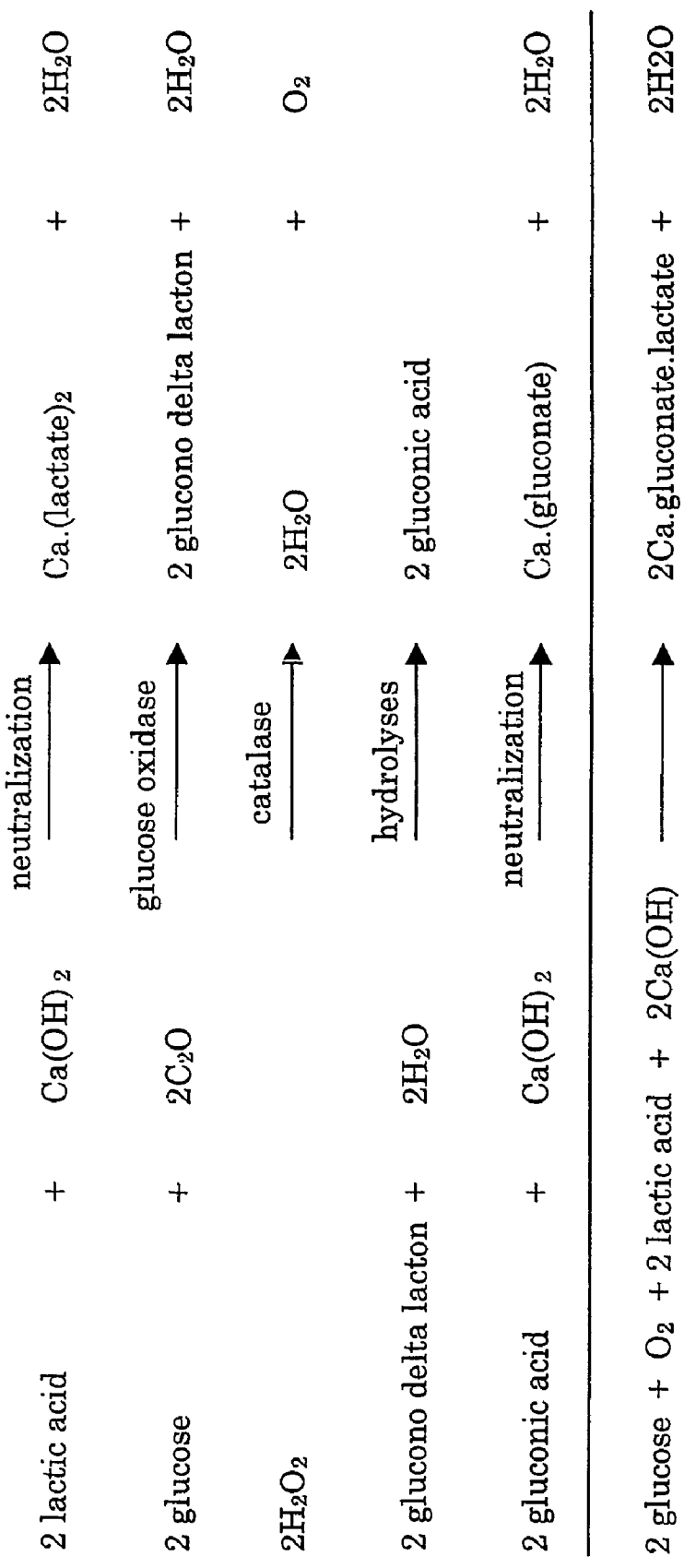
FIG. 1 shows the reaction equations involved in the production of calcium gluconate according to an embodiment of the present invention.

The present invention provides for a method for the preparation of calcium gluconate comprising enzymatic conversion of glucose to gluconic acid via glucono-delta-lactone, followed by conversion of gluconic acid to calcium gluconate in a reaction mixture to which a calcium base is administered and which further comprises a salt of an organic acid which is acceptable for use in foodstuffs, and water. An advantage of the new method is that the reaction conditions result in very high yields of calcium gluconate per unit of production volume without the formation of calcium gluconate crystals.

It has been found that in principle the use of any salt of an organic acid which may be used in foodstuffs leads to the advantages of the invention. By the phrase "acceptable for use in foodstuffs" is meant that consumption by humans or animals by intake in foodstuffs does essentially not lead to detrimental effects. In general, the phrase refers to essentially non-toxic salts. Specific examples of suitable salts include lactate salts, citrate salts, malate salts and combinations thereof. In the following description, the invention is illustrated by reference to lactate salts. This should under no circumstance by interpreted as restrictive with respect to the use of other salts in the context of the invention. Although very favorable results have been obtained using a lactate salt, other salts of organic acids lead to principally similar results.

The present invention provides for the first time an industrially attractive method for the enzymatic preparation of calcium gluconate. The method requires no sodium-calcium ion exchange procedures and no post-production purification of the product. The present invention relates to a new selective process for producing high-purity and high-soluble calcium gluconate in the presence of one or more lactate salts.

The present inventors have demonstrated inter alia that when prepared from glucose by an enzymatic reaction in the presence of calcium lactate, calcium gluconate exhibits solubility in excess of 225 g/kg solution at 20° C. This is considerably higher than the solubility of calcium gluconate produced by an enzymatic reaction in the absence of calcium lactate (30 g/L at 20° C.) and results in clear solutions without crystals and with a total calcium content in excess of 46 g total calcium/kg solution. The enzymatic yield of calcium gluconate in the reaction mixture according to the present invention may reach particularly high levels when the enzymatic conversion results in a mixture of 65 weight % of calcium gluconate and 35 weight % of calcium lactate. Considerably lower or considerably higher amounts of calcium lactate present in the reaction mixture will result in lower amounts of calcium gluconate produced per kg of reaction mixture. However, the mere presence of lactate salts during the enzymatic conversion of glucose into gluconic acid allows for the build-up of advantageously high amounts of calcium gluconate in the reaction mixture without the formation of calcium gluconate precipitates. Furthermore, the calcium gluconate produced according to a method of the invention is essentially pure and does not require additional purification steps. The presence of lactate salts in the reaction product does not limit the application of the calcium gluconate as a registered calcium fortificant, as lactate salts themselves is a registered food compound. Therefore, the lactate salts in the reaction product do not need to be removed or separated from the calcium gluconate product. The presence of additional metal salts of lactate is beneficial to the application of the calcium gluconate produced by a method according to the invention as a food fortificant since additional micronutrients may be provided in the form of lactate salts.

The enzymatic process uses a mixture of the enzymes glucose oxidase and catalase to convert glucose into gluconic acid in the presence of a lactate salt. During the enzymatic conversion, a calcium-base (e.g. calcium oxide, calcium hydroxide and/or calcium carbonate) is used for the purpose of neutralizing the evolving gluconic acid and to serve as a calcium source. The presence of the lactate salt(s) during the enzymatic reactions prevents the crystallization of calcium gluconate and/or calcium lactate and so high final concentrations (even above 360 g of combined dissolved calcium gluconate-calcium lactate per kg of reaction mixture) can be reached.

The present invention concerns a process for producing calcium gluconate salt that can be used in food fortification applications.

The present invention provides for a new, effective and economical process for the production of calcium gluconate from glucose in the presence of lactic acid salts.

The invention relates inter alia to a method comprising the steps of preparing a mixture of glucose, enzymes and a lactate-salt in water, enzymatically converting glucose into gluconic acid converting gluconic acid into calcium gluconate through the addition of a calcium base.

The conversion is carried out by the combined action of a mixture of at least two enzymes, at least comprising glucose oxidase (EC 1.1.3.4) and catalase (EC 1.11.1.6). It is an aspect of the present invention that the enzymes may be from any suitable source and is commercially available. A convenient source of the enzymes is a microbial source such as a fungal source or a bacterial source. An enzyme preparation containing both glucose oxidase and catalase which can be used with benefit in the present invention is for instance OxyGO 1500 (Genencor Inc., USA) or Novozyme 771 (Novo Nordisk A/S, Denmark). Alternatively, a combination of a glucose oxidase preparation and a catalase preparation may be used. As gluose oxidase, glucose oxidase G9010 (Sigma, USA) is for instance available. A catalase enzyme that can be used with benefit in the present invention is for instance catalase T100 (Genencor Inc., USA). As an alternative for glucose oxidase, other enzymes may be used, such as hexose oxidase (EC 1.1.3.5) or glucooligosaccharide oxidase, or any other enzyme that catalyzes the oxidation of glucose with oxygen resulting in the reaction products gluconic acid and hydrogen peroxide.

The amounts of enzyme used in the reaction mixture can be preparations as to produce the compound of the invention in a desired time period. The source of the enzymes may be selected as to result in optimum conversion rates under the reaction conditions applied.

Glucose, used in the context of the present invention may be administered to the reaction mixture in a crystalline form or in the form of a syrup. The initial glucose concentration in the reaction mixture may be up to 180 g/l of the reaction mixture. Preferably, the initial glucose concentration in the reaction mixture prior to complete conversion into calcium gluconate is above 30 g/l of the reaction mixture.

The lactate salt present in the reaction mixture may be from any suitable source and may be any lactate salt such as an alkali metal salt and/or alkaline earth metal salt of lactate, such as a sodium, a potassium, a calcium and/or a magnesium salt or a combination thereof. The lactic acid salt may be administered to the reaction mixture as a crystalline lactate salt. Alternatively, the lactic acid may be administered as lactic acid in dissolved form and may be neutralized prior to the start of the enzymatic conversion reaction by any suitable base such as an alkali metal salt base and/or alkaline earth metal salt base, e.g. a calcium base.

In another aspect of the invention, the lactic acid salt my be obtained in advance by microbial fermentation of a carbohydrate followed by neutralization with a suitable base, such as an alkali metal salt base and/or alkaline earth metal salt base, e.g. a calcium base to obtain a suitable lactate salt. In such an embodiment according to the invention, a preferred carbohydrate is glucose. A microbial fermentation of such an embodiment of the invention may be carried out under conditions known in the art and with any microorganism capable of producing lactate from carbohydrate fermentation, such as from lactic acid bacteria. A preferred such microorganism is *Lactobacillus rhamnosus*.

The lactate salt may be present at the beginning of the conversion reaction at sufficient quantities to yield optimum calcium gluconate levels in the reaction mixture. Alternatively, the lactate salt or lactic acid may be administered in consecutive steps or continuously during the course of the reaction in order to maintain a certain ratio between gluconate and lactate.

The method of the present invention may be carried out in any type of reactor available to those skilled in the art. These may comprise laboratory or industrial-scale fermenters with automated pH, alkali addition and temperature controls, but they may also comprise static reactor vessels to which reactants are added as separate administrations. Additionally, stirrers may be applied in the reactor to facilitate proper mixing of the reactants. The reactants may be added in one step or they may be added in multiple steps. The reactants may also be added continuously to the reactor during the conversion reaction.

The reaction conditions that may be used in the context of the present invention can be varied as to yield a product with desired properties or to produce the substance of the invention in a desired time period. Reaction conditions that may be varied by the artisan include, but are not limited to temperature, pH, aeration level, oxygen tension, pressure, carbon dioxide level, viscosity, and the like.

Temperatures of the reaction mixture during the conversion reaction that can be used in the context of the present invention are those that support the proper functioning of the enzymes. Such temperatures may be chosen anywhere between 0° C. and 50° C. Temperatures that can be used with benefit are between 30° C. and 40° C. Temperatures of the conversion reaction during industrial production of calcium gluconate according to a method of the invention may be optimized to result in high conversion rates by the enzymes and to result in high solubility levels of produced calcium gluconate.

The pH of the reaction mixture during the conversion may be regulated, i.e. controlled, by the addition of one or more bases and to such a value as to support the proper functioning of the enzymes. Primarily, said one or more bases are administered during the course of the conversion reaction to maintain proper pH values that support the proper functioning of the enzymes. They may also be administered prior to the start of the enzymatic conversion reaction. Suitable bases used in the context of the present invention for neutralization of evolving gluconic acid include alkali metal anions and/or alkaline earth metal anions.

An additional function of the base(s) added to the reaction mixture during the course of the conversion reaction may be to provide a calcium source for the calcium gluconate. This calcium source may be administered at once prior to the start of the enzymatic conversion reaction or continuously during the reaction. For this calcium source, a calcium base can be used with great benefit, although other calcium sources may also be used. The calcium base used as a calcium source may be identical to the base(s) used to maintain proper pH values, but it may also be a different base. Preferably, the neutralizing base(s) is (are) (a) calcium base(s) such as a calcium carbonate. Most preferable, the calcium base is calcium hydroxide.

In a preferred embodiment according to the invention, the calcium base is administered in an amount sufficient for the production of an amount of calcium gluconate in excess of 30 g/L of the reaction mixture, which is equivalent to a calcium ion concentration of in excess of 3.1 g/L at 20° C. derived from calcium gluconate alone. The total amount of calcium base administered to the reaction mixture is equivalent to a calcium ion concentration of in excess of 3,6 g/L at 40° C. derived from calcium gluconate alone.

The reaction may be unbuffered or buffered by using suitable buffers available to the skilled artisan. During the conversion reaction, the pH of the reaction mixture is preferable maintained between 3 and 9, more preferably between 4 and 6.

Aeration may be achieved by bubbling with oxygen or another appropriate oxygen source, such as air. The oxygen tension in the reaction mixture may be increased by using overpressure in the reactor. A dissolved oxygen tension (DOT) that can be used with benefit is preferably above 50%, more preferably, above 70%, most preferable above 80%.

The progress of the conversion may be followed by monitoring consumption of reactants such as the amount of neutralizing base added to the reactor vessel or by monitoring the oxygen consumption rate. The reaction can be stopped when sufficiently high levels of gluconic acid are produced or may be left running until all glucose is converted.

After completion of the conversion, or when sufficient calcium gluconate is produced, the enzymes are preferable removed from the reaction mixture. Removal of the enzymes from the reaction mixture may occur by any suitable methods known to the art. In a preferred embodiment according to the invention, the enzymes are inactivated and precipitated by heating to a temperature in excess of 40° C., preferably in excess of 50° C. Removal of the precipitated enzymes may occur by centrifugation. Enzyme precipitates can be removed with great benefit by filtration.

The clear and enzyme-free reaction mixture containing the calcium gluconate may then be dried to obtain the gluconate salt. In a preferred embodiment according to the invention, the liquid containing the calcium gluconate is spray dried using methods known to the art. In another preferred embodiment according to the invention, a calcium gluconate salt is obtained as a dry mixture of a gluconate salt and a lactate salt of calcium. Optionally, said mixture may be decolorized by methods known to the skilled artisan.

A method according to the invention may lead to mixtures of gluconate salts and salts of an organic acid which is acceptable for use in foodstuffs in a weight ratio from 5:95 to 95:5.

Specific advantageous examples of these mixtures include mixtures of calcium gluconate and calcium lactate, of calcium gluconate and magnesium lactate, of calcium gluconate and calcium citrate, of calcium gluconate and magnesium citrate, of calcium gluconate and calcium malate, and of calcium gluconate and magnesium malate. Also, it is possible to use one or more organic acids with their mineral base in the reaction mixture, added either during the enzymatic reaction or afterwards. If desired, however, the calcium gluconate prepared according to the invention may be purified further, e.g. by removal of the salt of an organic acid which is acceptable for use in foodstuffs.

The invention will now be illustrated by the following non-limiting examples.

EXAMPLES

Analytical Methods

Analyses

Calcium and magnesium were determined by Atomic Absorption Spectrometry. Gluconate and lactate were measured by HPLC. Reducing sugars were assayed according to Luff Schoorl displayed as % glucose/g dry weight. Refractive index was measured according to the Brix scale.

Glucose Oxidase—Catalase (GOC/Cat)

In all experiments the commercial preparation—OxyGO 1500—from Genencor International was used. This enzyme preparation contained, ≧1500 titrimetric units glucose oxidase/ml and ≧400 Baker units catalase/ml, according to the manufacturer.

Enzymatic Reaction Conditions

All enzyme reactions were carried out in laboratory fermenters (Applikon) with automated, pH controlled, alkali addition (set point pH=5.0) and temperature control set at 35° C. DOT (dissolved oxygen tension) was set at 80% by automated control of airflow (1-2 liter/min) and impeller speed (600-1250 RPM). The reaction was monitored by the rate of oxygen and alkali consumption.

Example 1

Preparation of Calcium Gluconate/Lactate

A solution was prepared by adding 237.6 g glucose.$H_2O$, 60 g lactic acid (90%) and 516.6 g demineralised water to the fermenter. With automated pH control and a 10% (w/v) suspension of $Ca(OH)_2$, the lactic acid was neutralised, until pH 5.0 was reached. A total of 180 ml $Ca(OH)_2$ was required.

The enzyme reaction was started by addition of 3.0 ml GOD/Cat and an instantaneous consumption of oxygen and alkali caused by the oxidative conversion of glucose into gluconic acid occurred. During the enzyme reaction, a 10% (w/v) suspension of $Ca(OH)_2$ was used to neutralize the evolved gluconic acid. After 11.5 hrs the reaction was completed, as indicated by the ceasing of alkali and oxygen consumption. During the enzyme reaction 462 ml of $Ca(OH)_2$ was consumed. After that, inactivation of enzyme was carried out by heating the reaction mixture during 30 min at 80° C., which resulted in precipitation of proteinaceous material, originating from the added enzyme preparation. Then, the liquid was cooled down to ambient temperature, the pH was set at 6.8 by addition of $Ca(OH)_2$. Subsequently, the mixture was filtered over a Seitz depth filter to remove the precipitated protein.

As a result, a clear, colorless liquid was obtained, containing calcium lactate gluconate. This 24° Brix solution contained 0.6 M calcium (24 g/L), 0.4 M lactate (36 g/L) and 0.8 M gluconate (156 g/L).

Above mentioned solution was spray dried and as a result, a white powder was obtained, which had the following composition:

| | |
|---|---|
| moisture | 3.62% |
| calcium | 10.26% |
| lactate | 658 mg/g as is |
| gluconate | 125 mg/g as is |
| reducing sugars | 0.23% |

Example 2

Preparation of Calcium Gluconate/Lactate

In a similar experiment, as mentioned in example 2, a higher concentration of calcium lactate gluconate was obtained during the enzyme reaction.

A solution was prepared by adding 279 g glucose.$H_2O$, 75 g lactic acid (90%) and 271 g demineralized water to a fermenter. Lactic acid was neutralized with 240 ml calcium hydroxide suspension. The enzymatic conversion was started by addition of 2.25 ml GOD/Cat and an extra addition of 0.1 ml of this enzyme was given after 18 hrs. The total enzymatic reaction time was 21 hours, during which 560 ml of $Ca(OH)_2$ was used to neutralize the gluconic acid produced.

The thus obtained solution contained 0.75 M calcium (30 g/L), 0.5 M lactate (44.5 g/L) and 1.0 M gluconate (195 g/L), and hence, containing approx. 270 g/L dry matter.

After heating and filtration, as mentioned in example 2, the liquid was stored overnight at 4° C., without any visual indication of crystallization. Subsequently, the solution was spray dried, resulting in a white powder of the following composition which had a composition approximately the same as mentioned in example 2.

Example 3

Preparation of Calcium Gluconate/Magnesium Lactate

An amount of 349.2 g glucose. $1H_2O$, 140.4 g lactic acid (90%) and 688 g demineralized water were added to the fermenter. With automated pH control and a 20% (w/v) suspension of $Mg(OH)_2$, the lactic acid was neutralized, until pH 5.0 was reached. 204 g $Mg(OH)_2$ suspension was required for lactic acid neutralization.

The enzyme reaction was started by addition of 3.0 ml GOD/Cat. During the enzyme reaction a 20% (w/v) suspension of $CaCO_3$ was used to neutralize the evolved gluconic acid. After 19.5 hr an extra 0.5 ml glucose oxidase was added to the reactor, which was repeated at 21.5 and 22.5 hr. The reaction was completed after 24 hr, as indicated by the termination of alkali and oxygen consumption. During the enzyme reaction 386,1 ml of $CaCO_3$ was consumed.

After heating and filtration, as mentioned in example 2, the clear and colorless liquid was spray dried, resulting in a white powder of the following composition:

| | |
|---|---|
| moisture | 7.4% |
| calcium | 70.4 mg/g as is |
| magnesium | 22.8 mg/g as is |
| lactate | 161 mg/g as is |
| gluconate | 572 mg/g as is |
| reducing sugars | 0.23% |

Example 4

Calcium Lactate Fermentatively/Ca-gluconate Enzymatically

In a one vessel reaction, calcium lactate was made fermentatively from glucose, followed by an enzymatic conversion of glucose into calcium gluconate. To this end, a fermentation was carried out, using *Lactobacillus rhamnosus* strain ATCC 10863. To the fermenter were added 257.5 g glucose.$1H_2O$, 20 g yeast extract and water to a final volume of 2000 ml. The fermentation was initiated by addition of 100 ml of an overnight, anaerobically, grown preculture containing: *Lactobacillus rhamnosus* strain ATCC 10863, 4.6% glucose, 3% yeast extract, 2.5% $CaCO_3$ and 0.1% $MnCL_2.4H_2O$. During the fermentation the reaction temperature was set at 37° C., the pH was set at 5.7 using a 20% (W/V) $Ca(OH)_2$ suspension to neutralize the evolved lactic acid. The impeller speed was set at 100 RPM and no aeration was used. During the fermentation, 440 g $Ca(OH)_2$ suspension was used. After 24 hr the reaction was stopped by heating the reaction mixture during 30 min at 70° C., in order to inactivate the bacteria.

The subsequent enzymatic reaction was carried out by addition of 847.5 g glucose.$1 H_2O$, 452.5 g $H_2O$ and 8 ml GOD/Cat to the fermentation broth. Aeration was carried out as mentioned earlier (see: Enzymatic reaction conditions). After 22.5, 23.5 and 24.5 hr of enzyme reaction an extra portions of glucose oxidase were added of 2, 2 and 1 ml respectively. The reaction was finished at 26.5 hr. A total of 819.1 g $Ca(OH)_2$ suspension was used during the enzyme reaction.

The resulting broth was processed by centrifugation to remove bacterial biomass. The supernatant was heated at 80° C. for 30 min during which it was treated with 10 g/l activated carbon to decolorize the solution. After filtration through a Seitz depth filter, a clear, very slightly yellow liquid was obtained, which was spray dried.

The resulting white powder had the following composition:

| | |
|---|---|
| moisture | 4.6% |
| calcium | 103 mg/g as is |
| lactate | 156 mg/g as is |
| gluconate | 643 mg/g as is |
| reducing sugars | 0.29% |

Example 5

Preparation of High Lactate Ratio Ca-Gluconate-Ca-Lactate

A solution was prepared by adding 275 g glucose.H2O and 750 g demineralised water to a fermenter. The reaction was started by adding 3 ml GOD/Cat. Simultaneously, a 50% lactic acid solution (made by adding 274 g 90% lactic acid and 220 g demineralized water) was added slowly to the fermenter by pumping at a flow rate of 30 ml/hr. The addition of all lactic acid took 22 hours.

By means of automated pH control and a 25% (w/v) suspension of CaCO3, both the gluconic acid, produced by the enzyme reaction and the lactic acid which was slowly added, were neutralized and maintained at pH 5.0 throughout the whole process.

The enzyme reaction was completed after 28 hours as indicated by the ceasing of alkali and oxygen consumption. A total of 820 g Calcium carbonate suspension was added during the process. Then the pH of the solution was set at 7.0 and it was heated and filtered as mentioned in example 1.

The resulting clear and colorless solution contained 3.9 M calcium, 1.3 M lactate and 0.66 M gluconate (156 g/l calcium, 117 g/l lactate, 129 g/l gluconate).

Example 6

Preparation of Calcium Gluconate/Lactate/Citrate

According to the enzymatic reaction method of example 2, a highly concentrated solution of calcium gluconate and calcium lactate was made, containing approximately 28% dry substance. To this mixture activated carbon was added, which was then heated to 90° C. to inactivate and precipitate the enzymes. Subsequently, the mixture was cooled to 40° C.

To 2 kg of this mixture 250 g citric acid monohydrate and 200 g CaCO3 were added while continuously stirring. After the CO2 formation ceased, the solution was filtered over a Seitz depth filter. The resulting clear and almost colourless solution contained approx. 38% dry substance and had a pH of 5.2.

The solution was spray dried, resulting in a white powder (calcium gluconate/lactate/citrate). The powder had a moisture content of 7.2% and a calcium content of 15.3% based on dry substance. The powder was completely cold water soluble.

The invention claimed is:

1. Method for the preparation of calcium gluconate comprising enzymatic conversion of glucose to gluconic acid followed by conversion of gluconic acid to calcium gluconate in a reaction mixture to which a calcium base is administered in an amount sufficient for the production of calcium gluconate in excess of 30 g/L of the reaction mixture, and which further comprises at least one salt of an organic acid which is acceptable for use in foodstuffs and water, wherein the initial glucose concentration in the reaction mixture prior to complete conversion into calcium gluconate is above 30 g/L of the reaction mixture, and wherein said calcium gluconate is produced to concentrations higher than 40 g/L in the reaction mixture.

2. Method according to claim 1, wherein said enzymatic conversion is carried out using glucose oxidase and catalase.

3. Method according to claim 1, wherein said calcium gluconate is completely dissolved.

4. Method according to claim 1 wherein said calcium gluconate is produced to concentrations higher than 100 g/L in the reaction mixture and is completely dissolved.

5. Method according to claim 1 wherein said calcium gluconate is produced to concentrations higher than 200 g/L in the reaction mixture and is completely dissolved.

6. Method according to claim 1, wherein the at least one salt of an organic acid which is acceptable for use in foodstuffs is selected from the group consisting of lactate salts, citrate salts, malate salts, and combinations thereof.

7. Method according to claim 6, wherein the salt is a lactate salt.

8. Method according to claim 7, wherein the lactate salt is administered as a crystalline lactate salt.

9. Method according to claim 6, wherein a combination of gluconic acid, lactic acid, citric acid and a calcium base is used as the at least one salt of an organic acid.

10. Method according to claim 7, wherein said at least one lactate salt is obtained by neutralization of lactic acid with an alkali metal base and/or alkaline earth metal base.

11. Method according to claim 10, wherein said lactic acid is obtained by anaerobic microbial conversion of a carbohydrate.

12. Method according to claim 10, wherein said carbohydrate is glucose.

13. Method according to claim 1, wherein said at least one salt of an organic acid which is acceptable for use in foodstuffs is a calcium salt.

14. Method according to claim 1, wherein said enzymatic conversion is carried out at a temperature of between 0 and 50° C.

15. Method according to claim 14, wherein said enzymatic conversion is carried out at a temperature of between 30 and 40° C.

16. Method according to claim 1, wherein said enzymatic conversion is carried out at a pH of between 3 and 9.

17. Method according to claim 16, wherein said enzymatic conversion is carried out at a pH of between 4 and 6.

18. Method according to claim 1, wherein said calcium base is administered to the reaction mixture in an amount equivalent to a final calcium ion concentration of more than 3.6 g/L at 40° C. derived from calcium gluconate alone.

19. Method according to claim 1, wherein said calcium base is calcium hydroxide.

20. Method according to claim 1, wherein the enzymes are removed from the reaction mixture by heat precipitation followed by filtration.

21. Method according to claim 1, wherein said water is removed by spray drying to obtain a gluconate salt/organic acid salt mixture.

22. Method according to claim 21, wherein said gluconate salt/organic acid salt mixture is optionally decolorized.

23. Method for the preparation of calcium gluconate comprising enzymatic conversion of glucose to gluconic acid followed by conversion of gluconic acid to calcium gluconate in a reaction mixture to which a calcium base and at least one salt of an organic acid which is acceptable for use in foodstuffs and water are administered in an amount sufficient for the production of calcium gluconate in excess of 30 g/L of the reaction mixture, wherein the initial glucose concentration in the reaction mixture prior to complete conversion into calcium gluconate is above 30 g/L of the reaction mixture.

* * * * *